United States Patent [19]

Marcelli

[11] Patent Number: 5,339,834
[45] Date of Patent: Aug. 23, 1994

[54] INFUSION SITE COVER AND IMMOBILIZER

[76] Inventor: Eileen Marcelli, 25 DuBois Ave., Sea Cliff, N.Y. 11579

[21] Appl. No.: 103,329
[22] Filed: Aug. 6, 1993
[51] Int. Cl.$^5$ .......................... A61F 5/37; A61F 13/00
[52] U.S. Cl. .................................. 128/877; 128/878; 128/DIG. 6; 128/888
[58] Field of Search ................. 128/877–882, 128/892, 869, 846, DIG. 6, DIG. 26, 888; 604/174; 602/12

[56] References Cited

U.S. PATENT DOCUMENTS

| | | | |
|---|---|---|---|
| 3,010,452 | 11/1961 | Smith | 128/881 |
| 3,722,508 | 3/1973 | Roberts | 604/174 |
| 3,955,565 | 5/1976 | Johnson, Jr. | 602/12 |
| 4,517,971 | 5/1985 | Sorbonne . | |
| 4,561,857 | 12/1985 | Sacks . | |
| 4,633,863 | 1/1987 | Filips et al. | 128/846 |
| 4,887,616 | 12/1989 | Baijnath . | |
| 4,941,479 | 7/1990 | Russell et al. | 128/877 |
| 4,941,480 | 7/1990 | McLean et al. | 128/879 |
| 4,976,700 | 12/1990 | Tollini . | |
| 5,018,534 | 5/1991 | Grant | 128/877 |
| 5,083,575 | 1/1992 | Jones . | |
| 5,131,412 | 7/1992 | Rankin | 128/877 |

Primary Examiner—Robert A. Hafer
Assistant Examiner—Michael O'Neill
Attorney, Agent, or Firm—Collard & Roe

[57] ABSTRACT

A device for covering, protecting and providing ready access to an infusion or wound site on a patient's limb including a first cover with cushions for supporting the patient's limb. A second cover is placed over the patient's limb into contact with the lower cover. Connecting straps removably connect the upper and lower covers together to protect the infusion site while permitting ready access to the infusion site. The covers may be provided with sections of transparent material to view the infusion site without having to remove the device. The device may also be used to immobilize a joint, by strapping the covers together across the joint.

8 Claims, 3 Drawing Sheets

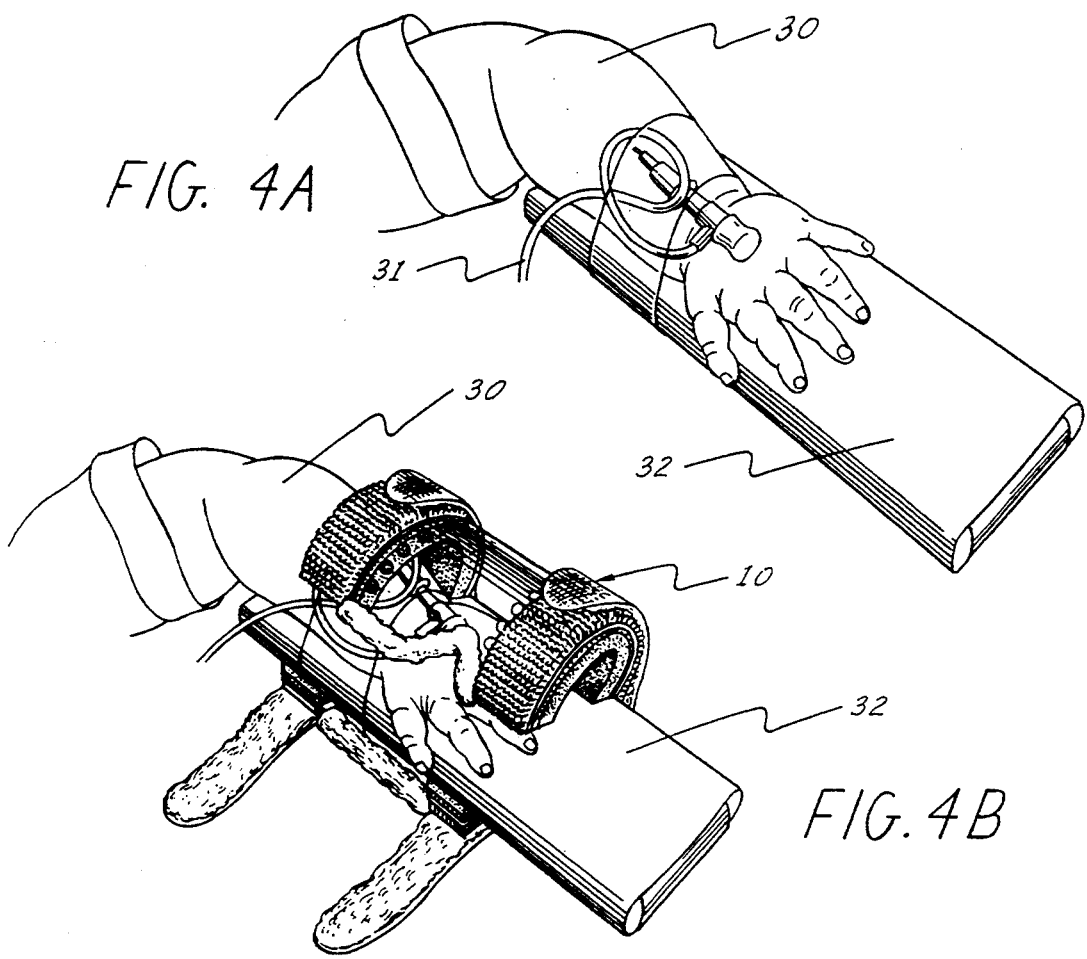
FIG. 4A
FIG. 4B
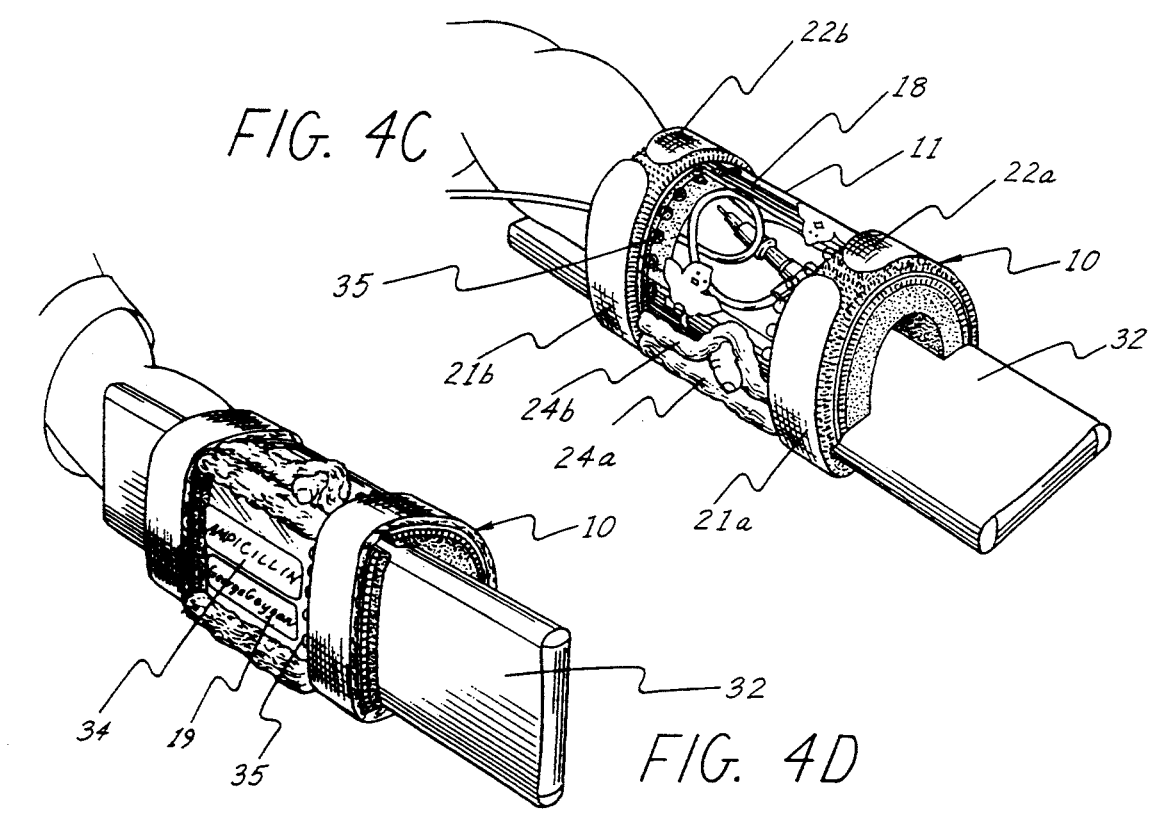
FIG. 4C
FIG. 4D

INFUSION SITE COVER AND IMMOBILIZER

CROSS-REFERENCE TO RELATED DOCUMENTS

The Applicant has previously submitted a Disclosure Document pertaining to this invention. The Disclosure Document was filed on Apr. 20, 1992 and received Disclosure Document No. 306,415.

BACKGROUND OF THE INVENTION

1. Field of the Invention

The invention relates to an infusion site cover and immobilizer that protects and provides ready access to an infusion site. More particularly, it relates to an infusion site cover and immobilizer which allows visual access to the infusion site through a transparent material and also functions as a joint immobilizer.

2. The Prior Art

When intravenous fluid is to be injected into a patient, the usual practice is to insert a cannula beneath the surface of the skin into a vein and then hold the cannula in position by adhesive tape. While this simple arrangement is effective, problems arise in that the adhesive tape often provides inadequate retention of the cannula as the patient moves or is moved. Accordingly, separate venipuncture site guard devices have been proposed to provide added protection to the infusion site. U.S. Pat. No. 3,722,508 discloses an infusion guard and immobilizer where the tubing is held within tubing clamp 19, as can be seen in FIG. 1. Since the tubing is held by the infusion guard, the tubing must be freed from the infusion guard each time the infusion guard is to be opened. A further drawback of the infusion guard is that it does not provide any cushioning between the patient's limb and the guard and it cannot be used if an arm board is already in place.

U.S. Pat. No. 4,517,971 to Sorbonne discloses a guard for a venipuncture site. However, a drawback exists with this patent in that cover 20 must be pivoted open, as can be seen in FIG. 5, each time the venipuncture site is to be examined. U.S. Pat. No. 4,561,857, U.S. Pat. No. 4,887,616, U.S. Pat. No. 4,941,479, U.S. Pat. No. 4,976,700 and U.S. Pat. No. 5,083,575 disclose various other types of intravenous equipment and related devices.

Therefore, it would be desirable to have an infusion site cover and immobilizer that provides cushioning between the device and the patient's limb and can be used with or without an arm board. It would be further advantageous to have an infusion site cover and immobilizer in which the infusion site can be visually inspected through a transparent section of the device. Lastly, it would be desirable to have an infusion site cover, wound cover and immobilizer that can be easily placed onto a patient to immobilize a limb, restrain the patient and prevent dislodgement or infiltration of an infusing I.V.

SUMMARY OF THE INVENTION

These and other related objects are achieved according to the invention by a device for covering, protecting and providing ready access to an infusion site on a patient's limb. The device includes a first cover including first cushioning means for resiliently supporting the patient's limb. A second cover has two spaced opposite ends with two edges defining an opening that extends between the two spaced opposite ends. The two edges contact the lower cover adjacent the patient's limb, with the patient's limb passing through the opening into the second cover. Connecting means movably and removably connect the upper and lower covers together to protect the infusion site while permitting ready access to the infusion site. The second cover may also include cushioning means for resiliently contacting the patient's limb.

The device includes means for visually inspecting the infusion site while covers are connected together, for example a section of transparent material. The first cover extends longitudinally, parallel to the patient's limb. The second cover is cylindrically shaped and has a central axis disposed parallel to the first cover and the patient's limb. The two edges extend parallel to the central axis. The two spaced opposite ends of the second cover are open, with the patient's limb passing through one of the open ends and the other open end providing ventilation to the infusion site.

The connecting means consists of one or more straps encircling the covers and securing the covers together. If more than one strap is utilized, the transparent material is ideally disposed between the two straps. The cushioning material is radially aligned with the straps.

The device will accommodate a patient's limb, for example an arm, with or without an arm board. Therefore, if the arm board is already in place, it need not be removed in order to take advantage of the device. The device may also be used for immobilizing a joint by having the first and second cover span the joint to be immobilized and then connected together.

BRIEF DESCRIPTION OF THE DRAWINGS

Other objects and features of the present invention will become apparent from the following detailed description considered in connection with the accompanying drawings which discloses an embodiment of the present invention. It should be understood, however, that the drawings are designed for the purpose of illustration only and not as a definition of the limits of the invention.

In the drawings, wherein similar reference characters denote similar elements throughout the several views:

FIG. 4A is a perspective view showing a patient's limb with an I.V. taped to an arm board;

FIG. 4B is a perspective view showing the first and second covers partially closed around the arm and arm board;

FIG. 4C is a perspective view showing the first and second covers completely closed around the arm and arm board; and FIG. 4D is a perspective view showing the bottom of the second cover containing patient information thereon.

DETAILED DESCRIPTION OF PREFERRED EMBODIMENTS

Figure 1:
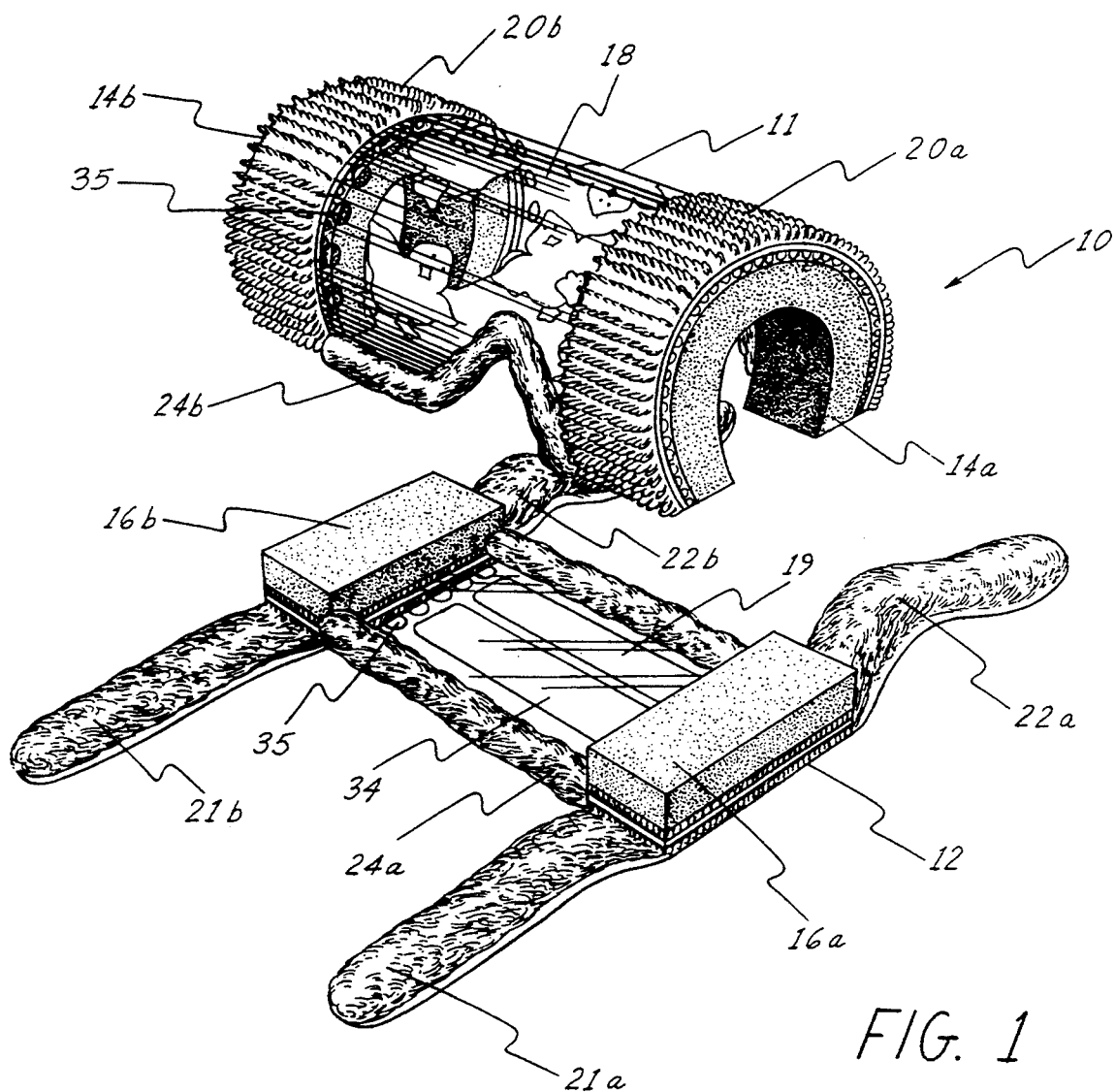
FIG. 1 is a perspective view of an embodiment of an infusion site cover and immobilizer according to the invention, showing the first and second cover separated from each other.
Figure 2:
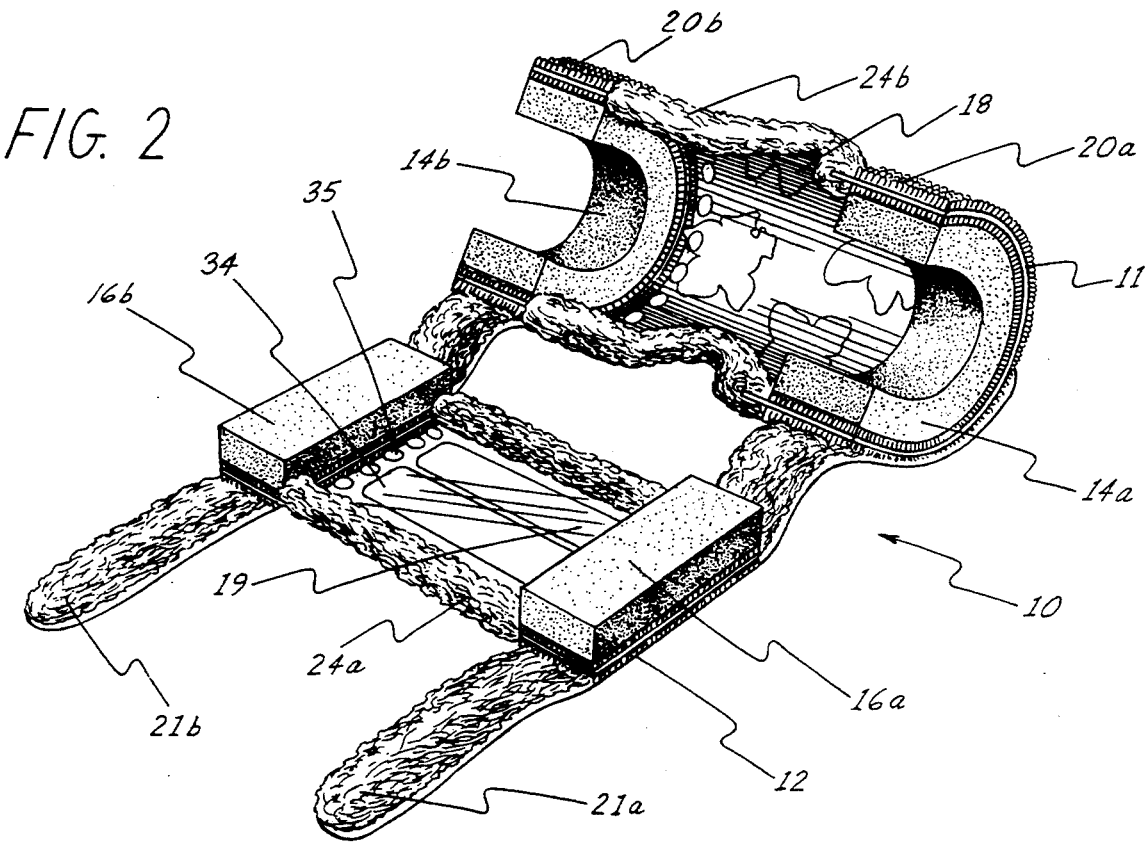
FIG. 2 is a perspective view of the infusion site cover and immobilizer with the first cover attached to one set of straps extending from the second cover.
Figure 3:
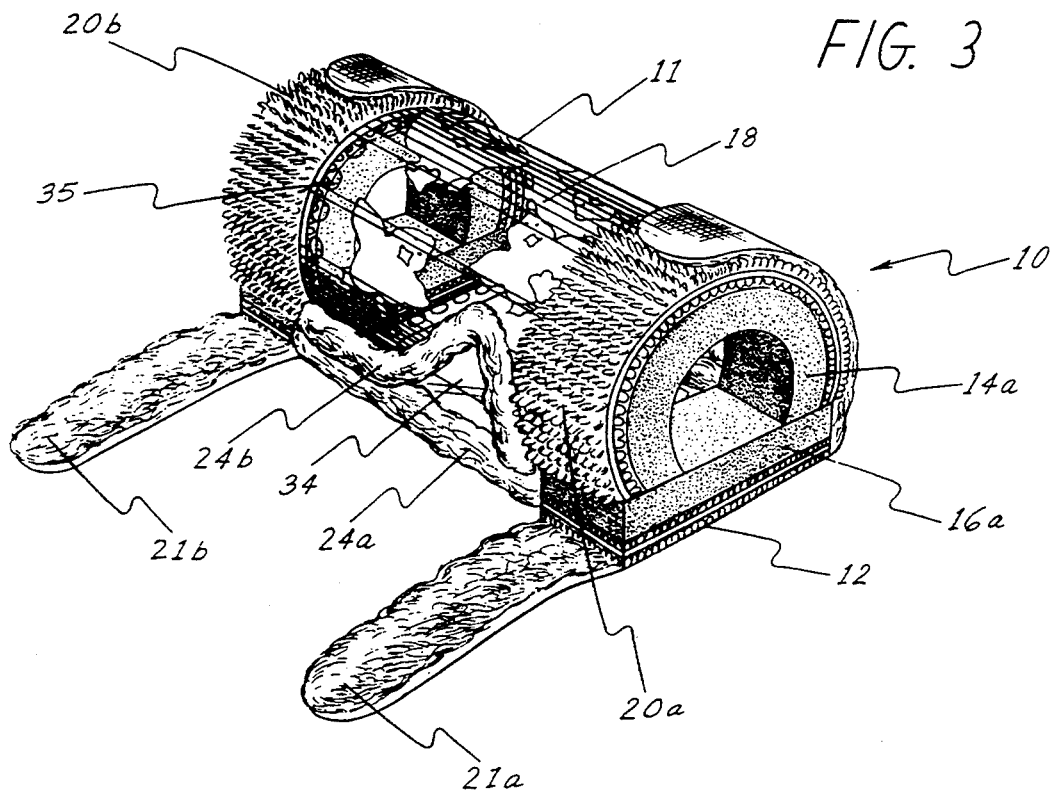
FIG. 3 is a perspective view showing the first cover in place against the second cover.

Referring now in detail to the drawings and in particular FIGS. 1, 2 and 3, there is shown an infusion site cover and immobilizer 10 having a first cover 11 and a second cover 12. First cover 11 is cylindrical or semi-cylindrical in shape and includes cushions 14A and 14B at either end thereof. Second cover 12 includes cushions 16A and 16B disposed generally below cushions 14A and 14B when the covers are placed together. In between the cushions, first cover 11 includes an arcuate shaped transparent material or window 18 and second cover 12 includes a planar transparent material 19, for example. Opposite cushions 14A and 14B are two strips of one part of a removable connector 20A and 20B, for example the loop portion of a hook and fastener. Opposite cushions 16A and 16B are straps 21A, 21B, 22A and 22B, for example the loop portion of a hook and loop fastener, which extend outwardly from second cover 12.

Straps 21 and 22 encircle first cover 11 to removably connect covers 11 and 12 together. The facing edges of first cover 11 and second cover 12 are lined with a soft material 24A and 24B, for example sheep skin or small soft split tubing.

In use, patient's arm 30, which has been set up with an I.V. catheter 31, is taped to an arm board 32, as can be seen in FIG. 4A. As per FIG. 4B, patient's arm 30 and arm board 32 are placed within the partially closed infusion site cover and immobilizer 10. As can be seen in FIG. 4C, first cover 11 is completely closed and is strapped to second cover 12 by straps 21 and 22. The infusion site is clearly visible through window 18. In the case of a pediatric patient, decals may be placed on window 18 as a distraction for the child. Window 18 includes a series of vent holes 35 located at either ends of both covers 11 and 12, for example. If the patient's hand is sufficiently large, a finger, for example a thumb, may extend outwardly of infusion site cover 10 where it would be cushioned between soft material 24A and 24B. As can be seen in FIG. 4D, a sticker 34 is placed on cover 12 that includes patient information so that the health care provider can rapidly determine what I.V. antibiotic or fluid a patient may be allergic to. Sticker 34 further includes the patient's name, since identification bracelets may be removed from the patient to avoid a tourniquet effect if the I.V. infiltrates.

Infusion site cover 10 can also be used without arm board 32 by simply placing the patient's limb between first cover 11 and second cover 12 with the infusion site positioned under window 18. Infusion site cover and immobilizer 10 may also be used to immobilize a joint or restrain a limb, with or without the presence of an infusion site thereon. As an immobilizer, cushions 14A and 16A would be located on one side of the joint, while cushions 14B and 16B would be located on the opposite side of the joint. Once first cover 11 and second cover 12 have been strapped together, the joint would be immobilized while the cushions 14 and 16 resiliently contact the patient, to provide maximum comfort and eliminate the possibility of further injury. As a restraint, the patient's hand would simply be placed into immobilizer 10 to prevent further injury during the recovery process.

While several embodiments of the present invention have been shown and described, it is to be understood that many changes and modifications may be made thereunto without departing from the spirit and scope of the invention as defined in the appended claims.

What is claimed is:

1. A device with an exterior and an interior for covering, protecting and providing ready access to a site on a patient's limb, the device comprising:
   a first longitudinally extending transparent planar cover with two spaced opposite ends and including first cushioning means disposed at each end thereof for supporting the patient's limb and soft material lining extending between said two spaced opposite ends;
   a second semi-cylindrical transparent cover having two spaced opposite ends with two edges defining an opening that extends between said two spaced opposite ends, said two edges being lined with a soft material and including at least one cushioned thumb hole, said two ends including second cushioning means for resiliently contacting said first cushioning means;
   decals placed on said transparent covers to distract the patient and a patient identification sticker placed on one of said covers; and
   connecting means comprising two straps encircling the exterior of the device and overlying said first and second cushioning means disposed on the interior of the device for movably and removably connecting said first and second covers together to protect the site, permit ready access to the site, and allow visual inspection of the site while said covers are connected together.

2. The device according to claim 1, said first cover extending longitudinally, parallel to the patient's limb; and
   said second cover having a central axis disposed parallel to said first cover and the patient's limb.

3. The device according to claim 2, wherein said two edges extend parallel to said central axis.

4. The device according to claim 3, wherein said second cover two spaced opposite ends are open ends.

5. The device according to claim 1, wherein said first cushioning means comprises:
   two lower strips of cushioning material, each of said lower strips being aligned with a respective one of said two straps.

6. The device according to claim 5, wherein said second cushioning means comprises:
   two upper strips of cushioning material, each of said upper strips being aligned with a respective one of said two straps.

7. The device according to claim 1, wherein
   said first cover adapted to span a joint with a part of said first cushioning means disposed on either side of the joint;
   said second cover adapted to span the joint with a part of said second cushioning means disposed on either side of the joint; and
   said straps are adapted to be disposed on either side of the joint to immobilize the joint.

8. The device according to claim 1, additionally comprising
   an elongated planar board adapted to be strapped to the limb to immobilize an infusion site, said board being disposed within the interior of the device.

* * * * *